(12) United States Patent
Qiao et al.

(10) Patent No.: US 11,592,429 B2
(45) Date of Patent: Feb. 28, 2023

(54) OPEN-AIR CIRCULATING POOL FOR SIMULATING ECOLOGICAL DAMAGE

(71) Applicant: China Waterborne Transport Research Institute, Beijing (CN)

(72) Inventors: Bing Qiao, Beijing (CN); Junya Duan, Beijing (CN); Bofan Yu, Beijing (CN); Tao Li, Beijing (CN); Mingbo Chen, Beijing (CN); Shan Hong, Beijing (CN); Sitang Hu, Beijing (CN); Ruiting Zhang, Beijing (CN); Cheng Dong, Beijing (CN)

(73) Assignee: China Waterborne Transport Research Institute, Beijing (CN)

( * ) Notice: Subject to any disclaimer, the term of this patent is extended or adjusted under 35 U.S.C. 154(b) by 0 days.

(21) Appl. No.: 17/321,357

(22) Filed: May 14, 2021

(65) Prior Publication Data
US 2022/0065837 A1    Mar. 3, 2022

(51) Int. Cl.
*G01N 33/18*    (2006.01)

(52) U.S. Cl.
CPC .................. *G01N 33/18* (2013.01)

(58) Field of Classification Search
CPC ........ G01N 15/02; G01N 15/06; G01N 33/18; G01N 33/1806; G01N 33/1866
See application file for complete search history.

(56) References Cited

U.S. PATENT DOCUMENTS

| | | | | |
|---|---|---|---|---|
| 5,167,802 A | * | 12/1992 | Sandstrom | G01N 1/18 436/39 |
| 5,823,714 A | * | 10/1998 | Chattey | E02B 3/06 405/195.1 |
| 2010/0212889 A1 | * | 8/2010 | Otsuka | E21B 47/103 166/250.01 |

FOREIGN PATENT DOCUMENTS

| | | | | |
|---|---|---|---|---|
| CN | 101551321 B | | 12/2011 | |
| CN | 103344411 B | * | 6/2015 | |
| CN | 105181919 B | | 1/2018 | |
| CN | 206891688 U | | 1/2018 | |
| CN | 106338589 B | * | 3/2018 | ............. G01N 33/18 |
| CN | 109596391 A | * | 4/2019 | ............. B63C 11/52 |
| CN | 110126993 B | * | 2/2020 | |

* cited by examiner

*Primary Examiner* — Judy Nguyen
*Assistant Examiner* — Martin Walter Braunlich
(74) *Attorney, Agent, or Firm* — Sheppard Mullin Richter & Hampton LLP

(57) ABSTRACT

The present disclosure provides an open-air circulating pool for simulating ecological damage, and belongs to the technical field of simulation tests of ecological environment impact. The open-air circulating pool is provided with a set of devices for simulating natural ecological environments of different water quality and sediments, as well as changes in water bodies caused by a sea occupation project, discharge of a typical pollution source and a sudden leakage accident, so as to observe changing trends of an aquatic organism and an environmental element, and qualitatively and quantitatively determine a law of causality of damage. The set of devices includes an open-air wave-flow circulating pool, an additive injection apparatus and an ecological indicator sampling and detection apparatus.

3 Claims, 1 Drawing Sheet

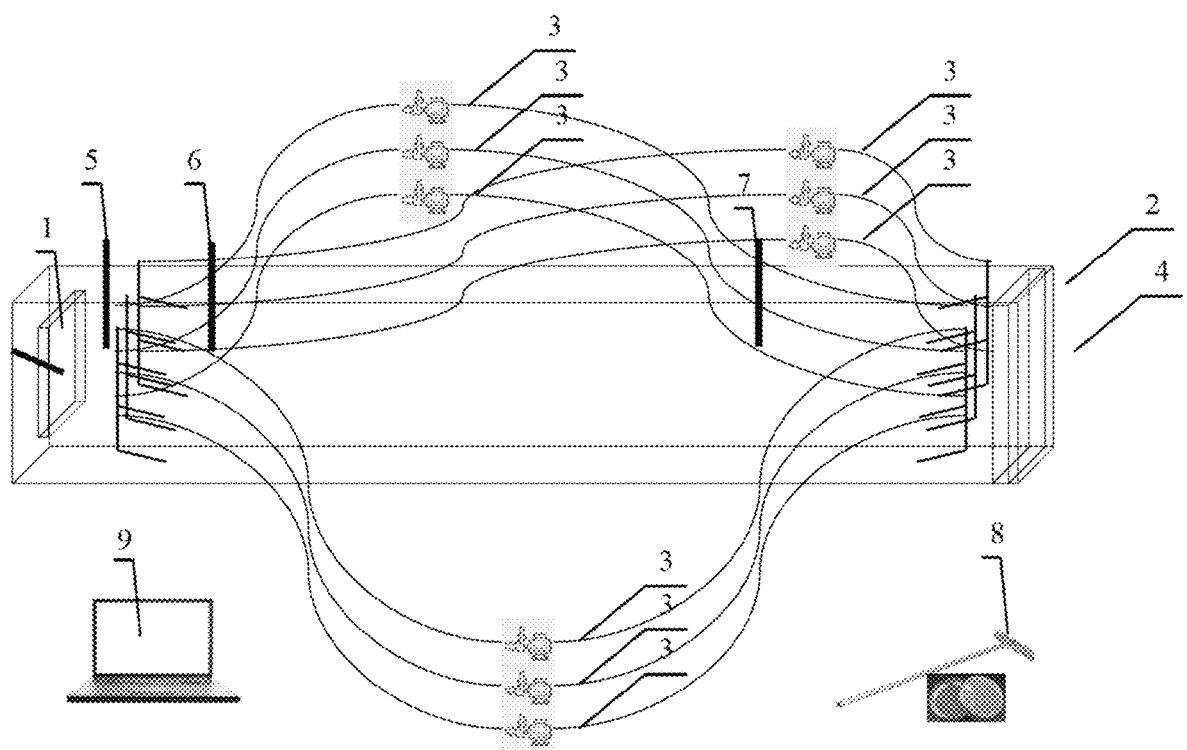

OPEN-AIR CIRCULATING POOL FOR SIMULATING ECOLOGICAL DAMAGE

CROSS REFERENCE TO RELATED APPLICATION

This patent application claims the benefit and priority of Chinese Patent Application No. 202010892738.9, on Aug. 31, 2020, the disclosure of which is incorporated by reference herein in its entirety as part of the present application.

TECHNICAL FIELD

The present disclosure relates to the technical field of simulation tests of ecological environment impact, in particular to an open-air circulating pool for simulating ecological damage.

BACKGROUND ART

In recent years, the ecological construction and ecological damage assessment and restoration in waterway transportation have attracted much attention. In order to scientifically identify the causality between the typical ecological damage source term and the ecological damage during the construction and operation of waterway transportation, it is necessary to test the ecological damage pathways, processes and interactions in a simulated environment. This will provide technical support for the in-depth understanding, prevention and mitigation of the ecological damage, as well as guidance on environmental planning, engineering construction, protection zone selection and environmental protection engineering design, etc.

At present, there is lack of an open-air circulating pool simulation system for ecological damage. The existing oil spill weathering simulation pools and test devices include: Wu Haitao et al., MARINE OIL SPILL WEATHERING SIMULATION SYSTEM, China, CN101551321B, 2011-12-28; Qiao Bing et al., TEST SYSTEM AND METHOD FOR SIMULATING IMPACT OF OIL SPILL WEATHERING ON WATER QUALITY, China, CN105181919B [P], 2018-01-19; Wu Xuan et al., WAVE TANK TEST DEVICE FOR OIL SPILL DISPERSANT, China, CN206891688U [P], 2018-01-16. They mainly simulate the weathering condition of the oil spill, the impact on water quality, and the cleanup effect, and never involve ecological impact simulation.

SUMMARY

I. Objective

In order to make up for the lack of ecological damage simulation equipment, the present disclosure provides an open-air circulating pool for simulating typical ecological damage in waterway transportation. The present disclosure employs a rectangular circulating pool in an outdoor environment to simulate natural ecological environments of different water quality and sediments, as well as changes in water bodies caused by a sea occupation project, the discharge of a typical pollutant and a sudden leakage accident. The present disclosure makes it possible to observe changing trends and laws of an aquatic organism and an environmental element in an open-air laboratory, and provides test support for qualitatively and quantitatively determining a causality of damage.

II. Technical Solution

In order to solve the technical problem, the present disclosure adopts a technical solution as follows: an open-air circulating pool system for simulating ecological damage.

The above objective of the present disclosure is achieved by a technical solution as follows:

An open-air circulating pool for simulating ecological damage, including an open-air wave-flow circulating pool, an additive injection apparatus and an ecological indicator sampling and detection apparatus, where the open-air wave-flow circulating pool is rectangular; a wave-making push plate and a wave-absorbing material are respectively provided on both ends of the open-air wave-flow circulating pool along a long axis; water outlets and water inlets connected to water pipes and water pumps are respectively provided after the wave-making push plate and before the wave-absorbing material, which are used to generate a circulating water flow with water in the pool; a speed and frequency of the wave-making push plate for repeatedly pushing the water and a flow rate of the circulating water flow driven by the water pump may be adjusted by wave-flow control software according to a need of a simulation test;

the additive injection apparatus is able to inject an additive and a typical damage source term into the open-air wave-flow circulating pool to simulate and maintain an ecosystem, and includes: (1) a test sediment laying apparatus, (2) a test water injection apparatus, (3) an introduced algae culture solution injection apparatus, (4) a cement block crane and (5) a nutrient and pollutant injection apparatus;

the ecological indicator sampling and detection apparatus has functions of on-site detection and sampling detection of water quality, sediment and biological indicators.

Further, the water outlets and water inlets of the open-air wave-flow circulating pool are respectively arranged on upper, middle and lower layers, three (left, middle and right) on each layer; the water outlets and water inlets are respectively connected to corresponding water pipes and water pumps to generate water flow patterns of different spatial distributions.

Further, the water pumps in the open-air wave-flow circulating pool are screw pumps, which prevent a biological component in the water from being damaged in operation.

Further, the test sediment laying apparatus in the additive injection apparatus includes a set of tools for sieving, weighing and mixing sandy, muddy or sandy-muddy mixed materials according to a certain particle size and ratio, and laying the materials on the bottom of the open-air wave-flow circulating pool before test water is injected.

Further, the test water injection apparatus in the additive injection apparatus includes a tank truck provided with offshore seawater and river water intake and drainage pumps, a tap water connector and drainage pipe and a prepared seawater additive weighing device and container, which are selected according to a need of the test water; the test water is injected into the open-air wave-flow circulating pool through the drainage pipe, where prepared seawater is produced by injecting tap water, weighing and putting an additive into the container according to a ratio, and dissolving with water.

Further, the introduced algae culture solution injection apparatus in the additive injection apparatus includes a plurality of Erlenmeyer flasks, which are filled with an algae culture medium and an algae culture solution, and are used to inject an inoculated algae culture solution into the pool to prepare test water with a specific dominant species of algae.

Further, the cement block crane in the additive injection apparatus is a crane that lifts and places a certain shape of cement block to an appropriate position in the open-air wave-flow circulating pool to simulate a damage source term from a sea occupation project and ecological damage thereof.

Further, the nutrient and pollutant injection apparatus in the additive injection apparatus includes a set of containers with a controllable quantitative injection pump; the containers are respectively filled with nitrogen (N) and phosphorus (P) required for ecosystem maintenance, common pollutants such as oily sewage and ballast water from a ship, and common pollutants such as diesel oil leaking in a sudden accident; according to an ecosystem maintenance need and an ecological damage scenario of the simulation test, a working parameter of the controllable quantitative injection pump is set to respectively inject the nutrient and pollutant into the open-air wave-flow circulating pool regularly in an appropriate amount.

Further, an on-site detection apparatus of the ecological indicator sampling and detection apparatus does not need sampling, just directly puts a detection probe into the open-air wave-flow circulating pool to acquire water quality indicator data such as temperature, dissolved oxygen (DO), pH and electrical conductivity, so as to analyze ecological damage related to a simulated working condition and environment.

Further, a sampling detection apparatus of the ecological indicator sampling and detection apparatus puts a collector to a certain position in the open-air wave-flow circulating pool to draw a certain volume of water and collect a certain volume of sediment; the samples are sent to a laboratory for detection and analysis according to a standard method to acquire water quality, sediment and biological indicator data such as total nitrogen (TN), total phosphorus (TP), pollutant load, algae cell concentration, chlorophyll-a content, particulate matter concentration, biological composition and particle size distribution, so as to analyze a causality of ecological damage related to a simulated working condition and environment.

Preferably, flow parameters of the water flow pumps at different depths and positions in the open-air wave-flow circulating pool are controlled to simulate flow rate changes before and after the sea occupation project, so as to indirectly analyze the damage source term from the sea occupation project and ecological damage thereof.

Preferably, by controlling the sediment laying apparatus to change a material and particle size ratio of the sediment, a test water flow rate lower than a real water flow rate is possible to conduct a scale-down ecological damage simulation test, so as to greatly reduce a power consumption cost of circulating water flow simulation.

Preferably, changes in material and energy cycles of the ecosystem caused by the typical ecological damage source term and the causality thereof may be simulated by controlling the sediment laying apparatus and the test water injection apparatus to appropriately increase a proportion of a biological component in the sediment and in a suspended matter in water.

FIG. 1 shows a structure of the open-air circulating pool for simulating ecological damage.

III. Advantages and Effects

The present disclosure provides an open-air circulating pool for simulating impacts of sea occupation, continuous discharge of a pollutant from a ship and a sudden leakage accident in water transportation on water quality, an aquatic organism and a sediment. The present disclosure makes up for the blank in the large-scale open-air ecological damage simulation device, and can provide scientific, systematic and effective test support for ecological shipping development, emergency capacity building and damage assessment and identification.

BRIEF DESCRIPTION OF THE DRAWINGS

FIG. 1 shows an open-air circulating pool test system.

| Reference Numerals: | |
| --- | --- |
| 1. | wave-making push plate |
| 2. | wave-absorbing material |
| 3. | circulating water flow system |
| 4. | rectangular open-air pool |
| 5. | water injection apparatus |
| 6. | additive injection apparatus |
| 7. | sampling and detection apparatus |
| 8. | sediment laying apparatus |
| 9. | wave-flow control software |

DETAILED DESCRIPTION OF THE EMBODIMENTS

A 25 m×0.6 m×1.2 m rectangular open-air circulating pool test system with a push-plate wave making system and a screw pump circulating water flow system is first prepared. It includes a rectangular open-air pool, a controllable push-plate wave maker, a wave-absorbing material, a screw pump and controllable circulating water flow system, a basic water quality data detection device, a sampling device, an additive injection apparatus, and a water quality, sediment and biological indicator test and analysis device.

The push-plate wave making system uses a motor and a reducer to drive a wave making plate to reciprocate along a long axis of the rectangular open-air pool, generating stably 4 to 5 regular waves with a height of 0-0.2 m and a period of 0.5-2 s. The circulating water flow system is divided into fresh water and seawater systems. In the fresh water system, 9 small submersible screw pumps that can be driven by solar energy are fixed at different heights and different positions at one end of the pool. Water outlets are connected by pipes to different heights and different positions at the other end of the pool to generate a circulating water flow. The seawater system is provided with an external medium-sized anti-pollution screw pump driven by electricity. Water inlets and the water outlets are respectively connected to 9 water dividers (3 rows up and down, 3 in each row) to generate a circulating water flow.

A specific simulation test of the open-air circulating pool test system is as follows:

Step 1: Aquatic system preparation. Sea sand and seawater from coastal waters are sequentially put into the pool, and nutrients such as nitrogen (N) and phosphorus (P) are supplemented until total nitrogen (TN) and total phosphorus (TP) in the water are basically stable.

Step 2: Introduction of algae species. One of green algae, cyanobacteria or diatoms is introduced as a dominant species in the pool by inoculation, and a daily change in the TN and TP in the water is maintained at around 15%.

Step 3: Ecological damage simulation test.

(1) Sea occupation project damage test: Two fixed square cement blocks (0.5 m×0.5 m×0.5 m) are placed at front and back ends of the pool respectively, and a water flow rate is changed to investigate water quality and biological changes for 10 days each.

(2) Daily pollutant discharge test: Common pollutants (such as oily sewage from a ship and ballast water with an over-standard biological indicator) are selected and continuously injected for 10 days. The pollutants are monitored during injection and 5 days after the injection.

(3) Sudden leakage accident: Diesel is selected as a common pollutant from a sudden leakage accident and is injected in an appropriate amount. 1 kg of diesel is injected within 1 h, and after the injection, continuous observations are performed at 00:30, 1:00, 3:00, 5:00, 7:00, 9:00, 11:00, 15:00, 19:00 and 23:00.

Step 4: Detection.

The pH, dissolved oxygen (DO) and chlorophyll-a content of a test sample are detected with a quick detection device. The concentration and particle size distribution of a suspended matter are detected by a Coulter particle counter calibrated by a micro-fluidic chip particle counter. Other water quality, biological and sediment indicators are detected by conventional standard methods.

According to detection results, changing trends and laws of an aquatic organism and an environmental factor are observed and summarized. Further, the following are analyzed: the ecological damage mechanism of regional occupation, the ecological damage way of influencing factors that are superimposed and accumulated, and the ecological damage mechanism of pollutants on the water environment, plankton, microorganisms and sediment. This provides a test basis for qualitatively and quantitatively determining the type, process and degree of ecological damage.

What is claimed is:

1. An open-air circulating pool for simulating ecological damage, comprising a set of equipment for simulating ecological damage, wherein the set of equipment comprises an open-air wave-flow circulating pool, an additive injection device and an ecological indicator sampling and detection device, and wherein
    the additive injection device injects a sediment, test water, an algae, a cement block, a nutrient and a pollutant into the open-air wave-flow circulating pool to simulate, by a wave-flow circulating system of the open-air wave-flow circulating pool, natural ecological environments of different water quality and sediments, changes in water bodies caused by a sea occupation project, discharge of a typical pollution source and a sudden leakage accident;
    the ecological indicator sampling and detection device places:
        a collector to a first position in the open-air wave-flow circulating pool to collect a sample, wherein the sample is sent to a laboratory for detection and analysis according to a standard method to acquire water quality, sediment and biological indicator data, wherein the water quality, sediment and biological indicator data comprises total nitrogen (TN), total phosphorus (TP), pollutant load, algae cell concentration, chlorophyll-a content, particulate matter concentration, biological composition and particle size distribution; and
        a detection probe into the open-air wave-flow circulating pool to acquire water quality indicator data, wherein the water quality indicator data comprises temperature, dissolved oxygen (DO), pH and electrical conductivity;
    wherein the water quality, sediment and biological indicator data reflect changing trends of an aquatic organism and an environmental factor, and provide a test basis for qualitatively and quantitatively determining a law of causality of damage by the sea occupation project, the discharge of a typical pollution source and the sudden leakage accident; and
    the open-air wave-flow circulating pool comprises a rectangular open-air pool, a wave-making push plate, a wave-absorbing material, a circulating water flow system and wave-flow control software, wherein:
        the wave-making push plate and the wave-absorbing material are respectively located inside double ends of the rectangular open-air pool along a long axis;
        the circulating water flow system is divided into upper, middle and lower layers, wherein on each layer, water outlets and water inlets are respectively connected to water flow pumps and connecting pipes;
        the water outlets and the water inlets are respectively located at appropriate distances from a front end of the wave-making push plate and the wave-absorbing material;
        the wave-flow control software controls a speed and a frequency of the wave-making push plate for repeatedly pushing water and a flow rate of a circulating water flow driven by a water flow pump; and
        the water flow pump in the circulating water flow system is a screw pump.

2. The open-air circulating pool according to claim 1, wherein:
    the additive injection device comprises a test sediment laying device, a test water injection device, an introduced algae culture solution injection device, a cement block crane and a nutrient and pollutant injection device;
    the test sediment laying device comprises a set of tools for sieving, weighing and mixing sandy, muddy or sandy-muddy mixed materials according to a first particle size and ratio, and laying the materials on the bottom of the open-air wave-flow circulating pool before the test water is injected;
    the test water injection device comprises a tank truck provided with offshore seawater and river water intake and drainage pumps, a tap water connector and drainage pipe and a prepared seawater additive weighing device and container;
    the introduced algae culture solution injection device comprises a plurality of Erlenmeyer flasks filled with an algae culture medium and an algae culture solution;
    the cement block crane is a crane that lifts and places a certain shape of cement block to a second position in the open-air wave-flow circulating pool;
    the nutrient and pollutant injection device is a set of containers with a controllable quantitative injection pump, wherein the containers are respectively filled with nitrogen (N) and phosphorus (P), first pollutants from a ship, and second pollutants in a sudden accident;
    a working parameter of the controllable quantitative injection pump is set to inject the nutrient and pollutant into the open-air wave-flow circulating pool regularly in a first amount; and
    the test sediment laying device and the test water injection device adjust a proportion of a biological component in a particulate matter of a test sediment and in a suspended matter in the test water, which are injected into the open-air wave-flow circulating pool.

3. The open-air circulating pool according to claim 1, wherein:
   the ecological indicator sampling and detection device comprises an on-site detection device and a sampling detection device;
   the on-site detection device comprises the detection probe; and the sampling detection device comprises the collector, wherein the collector draws a first volume of water and collects a first volume of sediment.

* * * * *